United States Patent

Healy et al.

[11] Patent Number: 5,670,161
[45] Date of Patent: Sep. 23, 1997

[54] BIODEGRADABLE STENT

[76] Inventors: Kevin E. Healy, 2517 Asbury Ave., Evanston, Ill. 60201; Gary S. Dorfman, 11 Sea Ridge Dr., Saunderstown, R.I. 02874

[21] Appl. No.: 654,314

[22] Filed: May 28, 1996

[51] Int. Cl.$^6$ .................................................. A61F 13/00
[52] U.S. Cl. .................... 424/426; 424/422; 604/8; 604/154; 604/281; 128/656; 128/657; 128/658; 128/898
[58] Field of Search .......................... 424/422, 426; 604/8, 154, 281; 128/656, 657, 659, 898

[56] References Cited

U.S. PATENT DOCUMENTS

| | | |
|---|---|---|
| 4,776,337 | 10/1988 | Palmaz ................................. 128/343 |
| 5,085,629 | 2/1992 | Goldberg et al. ........................ 604/8 |
| 5,147,385 | 9/1992 | Beck et al. ............................. 623/1 |
| 5,464,450 | 11/1995 | Buscemi et al. ......................... 623/6 |

*Primary Examiner*—Thurman K. Page
*Assistant Examiner*—Kathryne E. Shelborne
*Attorney, Agent, or Firm*—Schiff Hardin & Waite

[57] ABSTRACT

An expandable, biodegradable stent for use within a body lumen comprises a hollow tube made from a copolymer of L-lactide and ε-caprolactone that is not plastically expandable at normal body temperatures, and that is expandable using thermo-mechanical means at a temperature between about 38°–55° C. using a balloon catheter. The invention also relates to a method of making such a stent and to a method of deploying such a stent within the body.

51 Claims, 5 Drawing Sheets

BIODEGRADABLE STENT

The present invention relates to a biodegradable stent that is capable of being absorbed by the human body, and that also may function as a drug or nutrient delivery system as a result of its biodegradable properties.

BACKGROUND OF THE INVENTION

Stents, including cardiovascular and biliary stents, are well-known as devices that are used to support a body lumen, such as an artery, vein, biliary duct, or esophagus. They may be employed as a primary treatment for a constriction of a body lumen (stenosis), or may be used following a medical procedure, such as angioplasty, used to remedy stenosis.

Conventional stents have taken two forms. First, there are the self-expanding stents that typically are made of metal, and that may include a biocompatible coating. Such stents are permanently implanted into the human body by deploying them on or through a catheter, although removable stents of this kind are known to the art. The stent, which may be woven, strutted, or wound like a spring, is placed in tension or compression along the inner or outer perimeter of the catheter, and percutaneously inserted into the body where it is guided to the site of implantation. The stent then is released from the perimeter of the catheter, or extruded from the interior of the catheter, where it expands to a fixed, predetermined diameter, and is held in position as a result of that expansion. Many different configurations of such self-expanding stents, and of catheters used to deploy such stents, are known to the art.

One variation on these self-expanding stents is illustrated in Kawai et al., U.S. Pat. No. 4,950,258. Kawai discloses the use of a spring-like coil of plastic having "shape memory." The stent is manufactured to a desired size from homopolymers or copolymers of lactide and/or glycolide, and then compressed under suitable conditions for insertion into the body. Thereafter, the stent is heated, and because of "shape memory," returns to its original (uncompressed) size.

A second type of stent commonly used in the field is expandable as a result of mechanical action by the surgeon. One such stent is disclosed in Palmaz, U.S. Pat. Nos. 4,733,665, 4,776,337 and 4,639,632. According to the Palmaz patents, an unexpanded stent is permanently implanted in the body by percutaneously inserting it into a vessel using a catheter, and guiding the stent to the site where it is to be permanently implanted. Upon reaching the site of implantation, the balloon portion of the catheter is expanded, and concomitantly a portion of the stent also is expanded solely as a result of the mechanical force applied by the expanding balloon, until the stent is sized appropriately for the implantation site. Thereafter, the expanded balloon is deflated, and the catheter is removed from the body, leaving the stent held permanently in position. The stents disclosed in Palmaz are made of a metal or a nondegradable plastic, and, to achieve compatibility with and in the body, the stent may be coated with a biologically-compatible substance.

Commercially available stents of the types described above exhibit undesirable characteristics that the art has sought to overcome. Self-expanding stents may be inappropriately sized for the sites where they are to be deployed, increasing the risk of rupture, stent migration, stenosis, and thrombosis as the stent continually tries to expand after deployment to its predetermined, optimal diameter. Conversely, a stent sized too small for the lumen may project into the lumen, thereby causing a primary or secondary obstruction or migration. Both self-expanding and expandable stents that are known in the art, because they are designed for permanent implantation in the body, increase the risk of restenosis, thrombosis or other adverse medical effects because of the risk of adverse reaction by surrounding tissue, adverse reaction by the material flowing through the body lumen (such as blood or blood products), and deterioration of surrounding tissue and/or the stent itself. The metals or alloys used for such stents, because they are believed to be biologically stable, also remain in the body for the patient's life, unless surgically removed at a later date along with surrounding tissue. Thus, these stents do not permit temporary placement within the body unless patient and surgeon are prepared to undertake a second procedure to remove the stent, which is difficult or impossible in most cases.

Conventional balloon-deployed stents, like that described by Palmaz, also require an extensively perforated structure that can be mechanically expanded intraluminally by a balloon catheter without applying forces that are potentially threatening to the surrounding tissue. Such perforations also permit cell growth to occur from the intima or media lining the lumen. Thus, for example, endothelial cells and smooth muscle fibroblasts migrate through the perforations inside and around stents like that shown in Palmaz. Such endothelial cell growth is desirable to the extent that the endothelial layer inhibits the formation of blood clots (thrombogenesis) by providing a blood-compatible surface. However, vascular smooth muscle cell migration and proliferation may be undesirable when it is uncontrolled (as in intimal hyperplasia) and results in the occlusion of the lumen that has been surgically opened by placement of the stent. Thus, stents such as that described by Palmaz may be undesirable when the risk of intimal hyperplasia is substantial. The benefits of a balloon-deployed stent therefore may not be realized in such circumstances. Moreover, to the extent that the design of stents such as those described in Palmaz are dictated primarily by mechanical considerations, such as the forces needed to open the stent, biological considerations (such as designing the stent to limit cell ingrowth and migration, for example) frequently play a secondary role or no role at all.

Still another disadvantage of existing stents is that the materials from which they are made are rigid, and therefore the compliance of the stents (i.e., the ability to control the flexibility of the material used to design stents for particular applications) is limited. This has the disadvantage of exposing patients to risks associated with the placement of a device that may exhibit a rigidity in excess of that needed for the particular application.

Most conventional stents also are capable of being used as drug delivery systems when they are coated with a biodegradable coating that contains the drug to be delivered. The amount of the drug that can be delivered, and the time over which it may be released, therefore may be limited by the quantity of coating employed.

Beck et al., U.S. Pat. No. 5,147,385, discloses the use of a degradable, mechanically expandable stent prepared from poly($\epsilon$-caprolactone) or similar polymers that melt between 45°–75° C., because the melted polymer may be expanded in such a manner as to adapt to the body lumen in which it is deployed. At the same time, because poly($\epsilon$-caprolactone) enters a liquid phase in the temperature range that Beck discloses (at about 60° C.), the ability to achieve controlled, improved strength characteristics using the stent described by Beck is limited. Furthermore, the temperature range described by Beck et al. is well-above the glass-transition temperature for poly(ε-caprolactone). This limits the ability of a stent made according to Beck et al. to resist radially compressive forces imparted by the lumen upon the stent without creeping or relaxing, introducing a substantial risk of occluding the lumen. Alternatively, one might use massive structures made according to Beck et al. to keep the lumen open, but in so doing, the normal function of the lumen would be perturbed significantly, possibly creating regions where flow of body liquids through the lumen would be severely restricted or stagnate, so that clots may form in those regions.

Slepian et al., U.S. Pat. No. 5,213,580, discloses an endoluminal sealing process using a poly(caprolactone) material that is flowable at temperatures above 60°–80° C. According to Slepian, this flowable material is able to conform to irregularities on the inner surface of the body lumen in which it is deployed.

Goldberg et at., U.S. Pat. No. 5,085,629, discloses the manufacture of a urethral stent made from a terpolymer of L-lactide, glycolide, and ε-caprolactone, which is selected to permit the stent to degrade within the body. Goldberg does not, however, disclose the use of an expandable stent, nor does Goldberg et al. provide any information regarding the design of the stent or its method of deployment within the body.

Thus, a stent that overcomes the problems just identified, while at the same time providing or enhancing the benefits that result from the use of stents, is needed to improve patient safety and recovery.

SUMMARY OF THE INVENTION

The present invention seeks to overcome those problems by providing an expandable, biodegradable stent for use within a body lumen. The invention consists in essence of a hollow tube made from a copolymer of L-lactide and ε-caprolactone that, in unexpanded form, is of a first diameter sufficient to be retained upon a balloon catheter for placement within the body lumen. The stent is not expandable at normal body temperatures. The stent is expandable using a thermally-assisted mechanical expansion process at a temperature between about 38°–55° C., to a second diameter sufficiently large to be retained in place within the body lumen. The invention also is found in a method of making that stent, and in a method of deploying such a stent within the body.

It is thus an object of the invention to provide a biodegradable stent that can be deployed in the body for a sufficient period of time to permit the site to be supported by the stent to heal, remodel, and grow strong, and thereafter to be absorbed into the body, thus reducing the risk of thrombosis or other adverse health effects associated with foreign materials in the body.

It is still another object of the invention to provide such a stent which can be deployed percutaneously by taking advantage of thermally-activated properties that permit the stent to be permanently deformed at temperatures just above normal body temperature, while remaining sufficiently rigid at body temperature to provide for mechanical support of the surrounding tissue.

Another object of the invention is to provide a stent that can be designed with a variable geometry and compliance to permit the designer and/or surgeon to tailor the characteristics of a particular stent to fit its application more precisely than is presently possible.

Still another object of the invention is to provide such a stent made from a material that permits the use of the stent as a drug delivery system to promote healing at the site of deployment. These and other objects of the invention are achieved as described below.

DETAILED DESCRIPTION OF THE INVENTION

Figure 1:
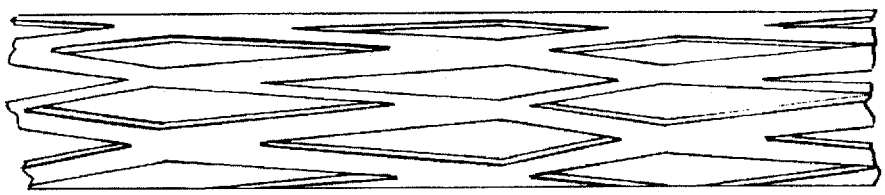
FIG. 1 is an illustration of an embodiment of an unexpanded stent according to the present invention.

The stent made according to the present invention comprises a cylindrical tube of appropriate size to be inserted into a body lumen, and thus typically is about 1–12 cm in length (and for vascular applications, most frequently 2–3 cm in length), and about 0.5–8 mm in diameter (for vascular stents, most frequently 1–3 mm in diameter). As shown in FIG. 1, the stent is a hollow tube of substantial length that is used to line the body lumen and provide support for keeping the lumen open, while at the same time limiting intimal hyperplasia by providing a finite number of perforations through which cells may migrate and occlude the body lumen in the region of the stent. This technique, which includes endoluminal paving, therefore is believed to be effective in limiting intimal hyperplasia.

Figure 2:
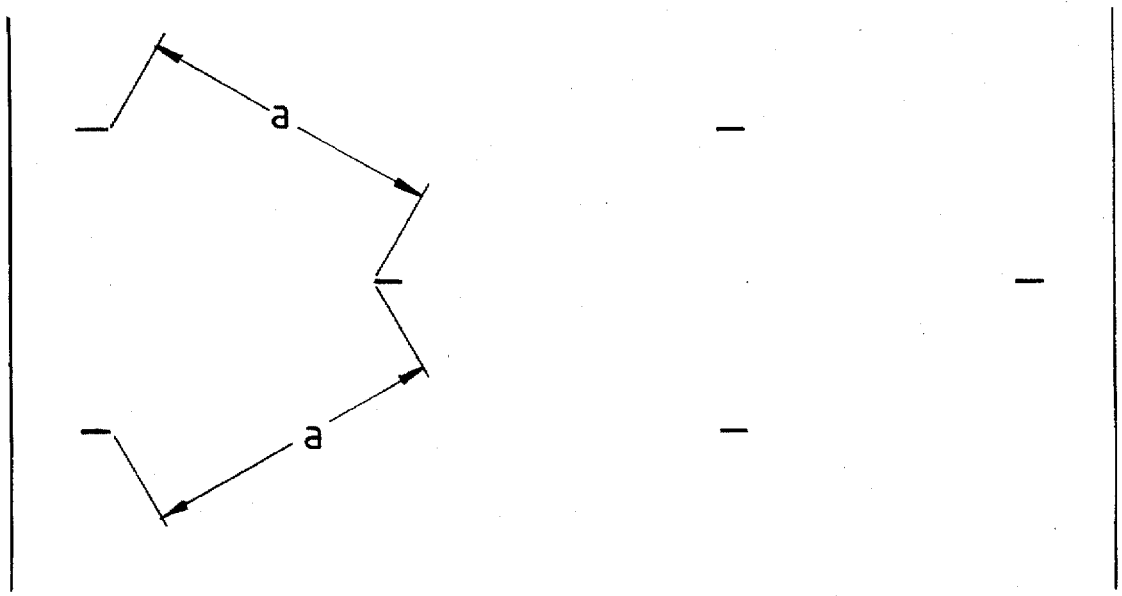
FIGS. 2–4 are plan drawings of various perforation patterns useful for stents made according to the invention.
Figure 3:
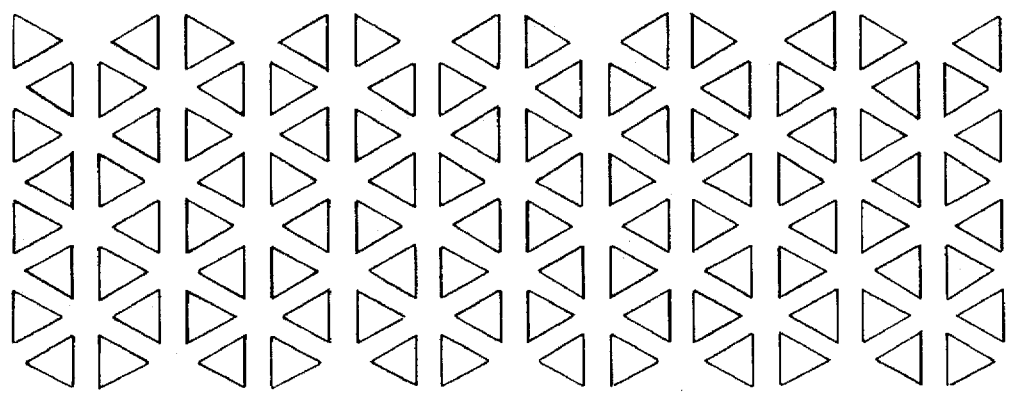
Figure 4:
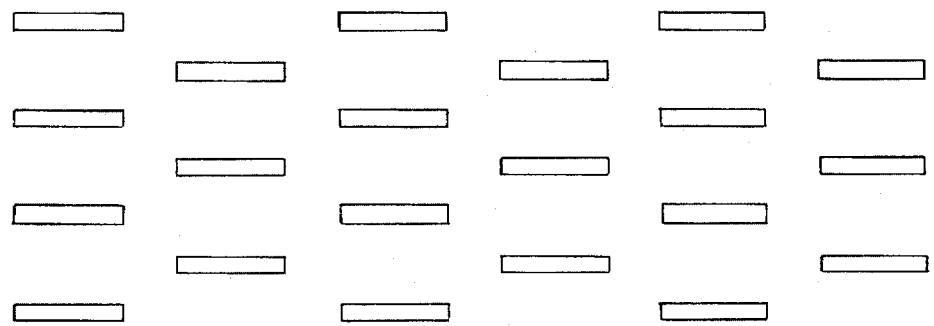

Endothelial coverage, in which the cells grow over and envelop the stent, is desirable in some cases because the stent may become a site for thrombosis, or clotting, to occur. As a result, it may be desirable to permit limited cell growth from the intima into the stent by providing perforations in the walls of the stent through which endothelial cells may grow and eventually cover all of the stent. Thus, as shown in FIGS. 2 through 4, the stent made according to the present invention may desirably incorporate perforations of different size and shape to permit the ingrowth of cells from the intima. In FIG. 2, a small perforation is provided in the walls of the stent at discrete intervals (designated by the letter "a") correlated to cell ingrowth in the particular body lumen. For example, a vascular stent having the design shown in FIG. 2 would be perforated at 2 mm intervals to accommodate cell ingrowth from the vascular intima, which has been shown to grow over this distance.

FIGS. 3 and 4 show perforation patterns that have been found desirable for expanding the stent intraluminally while maintaining significant hoop strength. Alternatively, the stent may be an imperforate tube.

Perforations in the walls of a stent made according to the present invention reduce the amount of material that must be heated to permanently deploy the stent. As a result, those perforations permit the stent to be deployed with a lesser amount of heat than if the stent were not perforated. This means that a perforated stent can be deployed using lower temperature heating devices, or with less heating time, or both, than if perforations were not present. (The stent still must be heated near or above the glass-transition temperature, as described below, to be expanded.) The size and shape of these perforations, the frequency of their placement along the walls of the stent, and the thickness of the stent material also control the total force required to expand the stent, and also to resist collapse after deployment. The characteristics of the perforations also affect the change in length of the stent as it is expanded. Finally, such perforations may be placed to accomplish desirable biological effects, such as control ingrowth or migration, at distances that maximize the ability to prevent lumen narrowing, and that also foster cell ingrowth for the particular body lumen. The design thus may be selected to optimize the mechanical properties required of the stent with the biological properties that are desired from the stent.

In a particularly preferred embodiment of the invention, a radio-opaque contrast material is incorporated into the stent, so that the location of the stent can be determined using conventional radiographic techniques. The radio-opaque material may take the form of a platinum wire or other similar radio-opaque structure that is molded into the stent or inserted through perforations in the stent. Alternatively, the radio-opaque material may take the form of fine particles of barium sulfate that are blended with the copolymer from which the stent is made; in this case, the radio-opaque material must not adversely impact the mechanical properties of the copolymer, and must be biocompatible.

Figure 5:
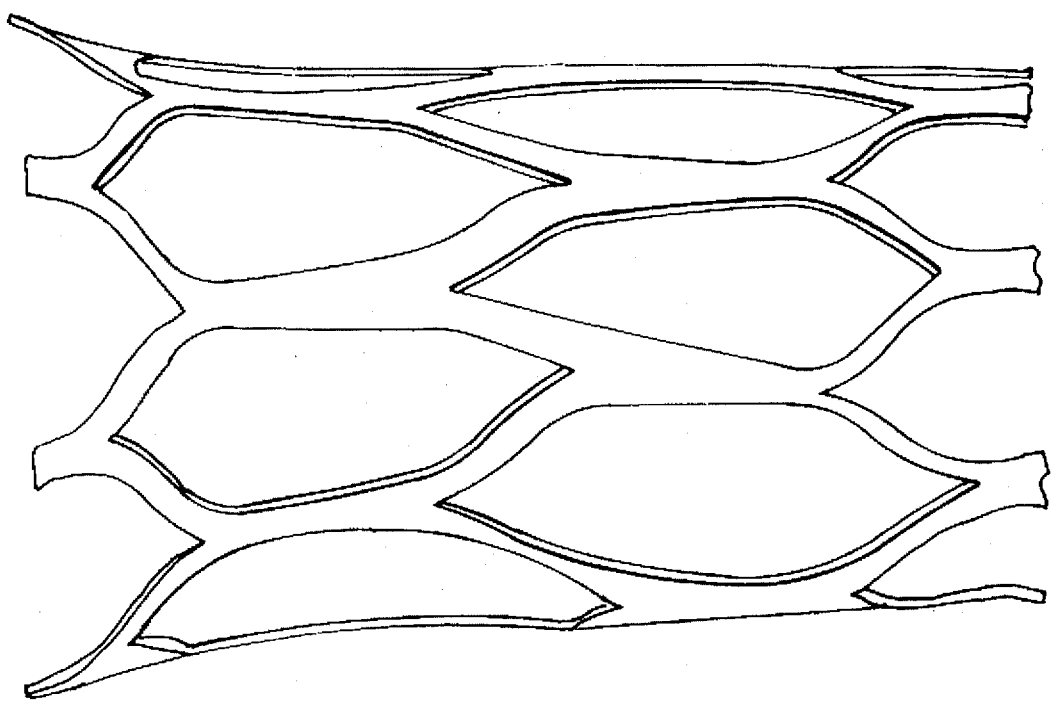
FIG. 5 is an illustration of the end portion of the stent of FIG. 1 after expansion.

When the stent is expanded, any perforations that are included in the stent also are expanded, and their shape is changed. This is illustrated in FIG. 5, which is an expanded version of the stent depicted in FIG. 1.

Regardless of the macrostructure of the stent, the stent of the present invention is prepared from a copolymer of L-lactide and ε-caprolactone in the molar ratios described below. In addition to the random copolymer, blends of either this copolymer (with different quantities of L-lactide and ε-caprolactone in each component of the blend) or of each homopolymer also may be used to achieve the desired thermal and mechanical properties in the final product. The L-lactide-ε-caprolactone copolymer is biodegradable, in that it is broken down over time by random hydrolysis within the body and metabolized without adverse consequence to the patient.

The relative amounts of each of L-lactide and ε-caprolactone in the copolymer are selected to produce thermal and mechanical properties that permit the copolymer to be thermo-mechanically expanded just above normal body temperatures, while remaining sufficiently rigid and strong at normal body temperatures to support the body lumen. Thus, when heated, the copolymer should be expandable near its glass-transition temperature, in the range of about 38°–55° C., but the copolymer should not melt (viz., become a flowable liquid) within the temperature range. (The exact glass-transition temperature will vary depending upon the relative composition of each component of the copolymer and other physical properties of the material.) In this context, thermo-mechanical "expansion" means that the polymer can be plastically deformed without fracture by increasing the inside and outside diameters of the stent under applied heat and mechanical force. Thus, in the useful temperature range, the copolymer undergoes a transition from a glassy state, in which the copolymer is strong and stiff, and exhibits less than about 3% elongation, to a rubbery state in which the material becomes elastic, leathery, pliable, and undergoes more than about 200% elongation. It is believed that if the temperature needed to expand the copolymer is significantly higher than 55° C., the heat needed to expand the copolymer may adversely affect the surrounding tissue by burning or otherwise damaging it, thereby interfering with healing following the deployment of the stent. At the same time, however, if the expansion temperature of the polymer is below about 38° C., there is a risk that the stent will soften in the body and collapse if the temperature rises as a result of fever or other similar circumstance. This creates a risk of restenosis or other adverse conditions resulting from collapse or deformation of the softened stent.

Some mechanical properties of the poly(L-lactide-ε-caprolactone) copolymer are set forth in Table 1. Thus, it is believed copolymers having a molar ratio of L-lactide to ε-caprolactone of about 90:10 to about 98:2 (as determined by conventional NMR analysis) are useful in the present invention.

TABLE 1

| L-lactide (mol %) | ε-caprolactone (mol %) | Melting Point (°C.) | Sample Temperature (°C.) | Modulus of Elasticity (MPa) | Strain (%) |
|---|---|---|---|---|---|
| 86 | 14 | 130–140 | 35 | 1134 | 372 |
| | | | 37 | 878 | 335 |
| | | | 40 | 818 | 347.3 |
| | | | 42 | 338 | 368.7 |
| | | | 45 | 148 | 382.5 |
| | | | 47 | 136 | 384 |
| | | | 50 | 17 | 411.3 |
| | | | 53 | — | 393.2 |
| 91 | 9 | 141–165 | 35 | 1916 | 2.8 |
| | | | 37 | 1690 | 2.8 |
| | | | 40 | 1809 | 115 |
| | | | 42 | 1432 | 151.7 |
| | | | 45 | 758 | 375.2 |
| | | | 47 | 1051 | 356.7 |
| | | | 50 | 352 | 381.7 |
| | | | 53 | 121 | 383.3 |
| 92 | 8 | 152–171 | 35 | 1309 | 3 |
| | | | 37 | 910 | 2.9 |
| | | | 40 | 1225 | 88.1 |
| | | | 42 | 1451 | 192.5 |
| | | | 45 | 591 | 318.7 |
| | | | 47 | 991 | 340.7 |
| | | | 50 | 499 | 324.3 |
| 93 | 7 | 155.5* | 35 | 1035 | 3.07 |
| | | | 37 | 1147 | 3.58 |
| | | | 40 | 1233 | 2.9 |
| | | | 42 | 1013 | 6.14 |
| | | | 45 | 1290 | 41.3 |
| | | | 47 | 1367 | 222 |
| | | | 50 | 1343 | 264 |
| | | | 53 | 529 | 294 |
| 93.5 | 6.5 | 155–172 | 35 | 1421 | 2.3 |
| | | | 37 | 1262 | 2.5 |
| | | | 40 | 1274 | 3 |
| | | | 42 | 1559 | 3 |
| | | | 45 | 1036 | 3.9 |
| | | | 47 | 1051 | 308.7 |
| | | | 50 | 543 | 335.7 |
| | | | 53 | 550 | 291.7 |
| 93.7 | 6.3 | 151.52* | 35 | 1064 | 2.68 |
| | | | 37 | 1006 | 2.55 |
| | | | 40 | 937 | 2.95 |
| | | | 42 | 1104 | 2.73 |
| | | | 45 | 1751 | 38.35 |
| | | | 47 | 1128 | 292 |
| | | | 50 | 787 | 326 |
| | | | 53 | 324 | 319 |
| 95.6 | 4.4 | 155.44* | 35 | 1471 | 2.68 |
| | | | 37 | 865 | 2.75 |
| | | | 40 | 788 | 2.83 |
| | | | 42 | 835 | 2.75 |
| | | | 45 | 916 | 74.00 |
| | | | 47 | 1192 | 194.00 |
| | | | 50 | 934 | 320.00 |
| | | | 53 | 779 | 330.00 |
| | | | 55 | 1572 | 297.00 |
| 97 | 3 | 156–178 | 35 | 1656 | 2.4 |
| | | | 37 | 1155 | 3.2 |
| | | | 40 | 1191 | 2.6 |
| | | | 42 | 1305 | 3.3 |

TABLE 1-continued

| L-lactide (mol %) | ε-caprolactone (mol %) | Melting Point (°C.) | Sample Temperature (°C.) | Modulus of Elasticity (MPa) | Strain (%) |
|---|---|---|---|---|---|
| | | | 45 | 1054 | 3.7 |
| | | | 47 | 1537 | 3.4 |
| | | | 50 | 1085 | 302 |
| | | | 53 | 1467 | 270.3 |
| 97.0 | 3.0 | 166.24* | 35 | 1628 | 2.53 |
| | | | 37 | 1141 | 3.16 |
| | | | 40 | 1120 | 2.98 |
| | | | 42 | 1003 | 3.30 |
| | | | 45 | 921 | 3.18 |
| | | | 47 | 980 | 74.00 |
| | | | 50 | 1019 | 356.00 |
| | | | 53 | 903 | 342.00 |
| | | | 55 | 713 | 318.00 |

The data set forth in Table 1 were obtained by performing tensile testing in a controlled temperature environment using thin samples (approximately 0.3 mm×6.35 mm×75 mm) of the L-lactide/ε-caprolactone copolymer. The strain and elastic modulus data presented are averages obtained from multiple tests of each material at each temperature. Melting point data were either determined by conventional DSC techniques or modulated DSC techniques (as denoted in Table 1 by an asterisk).

Figure 6:
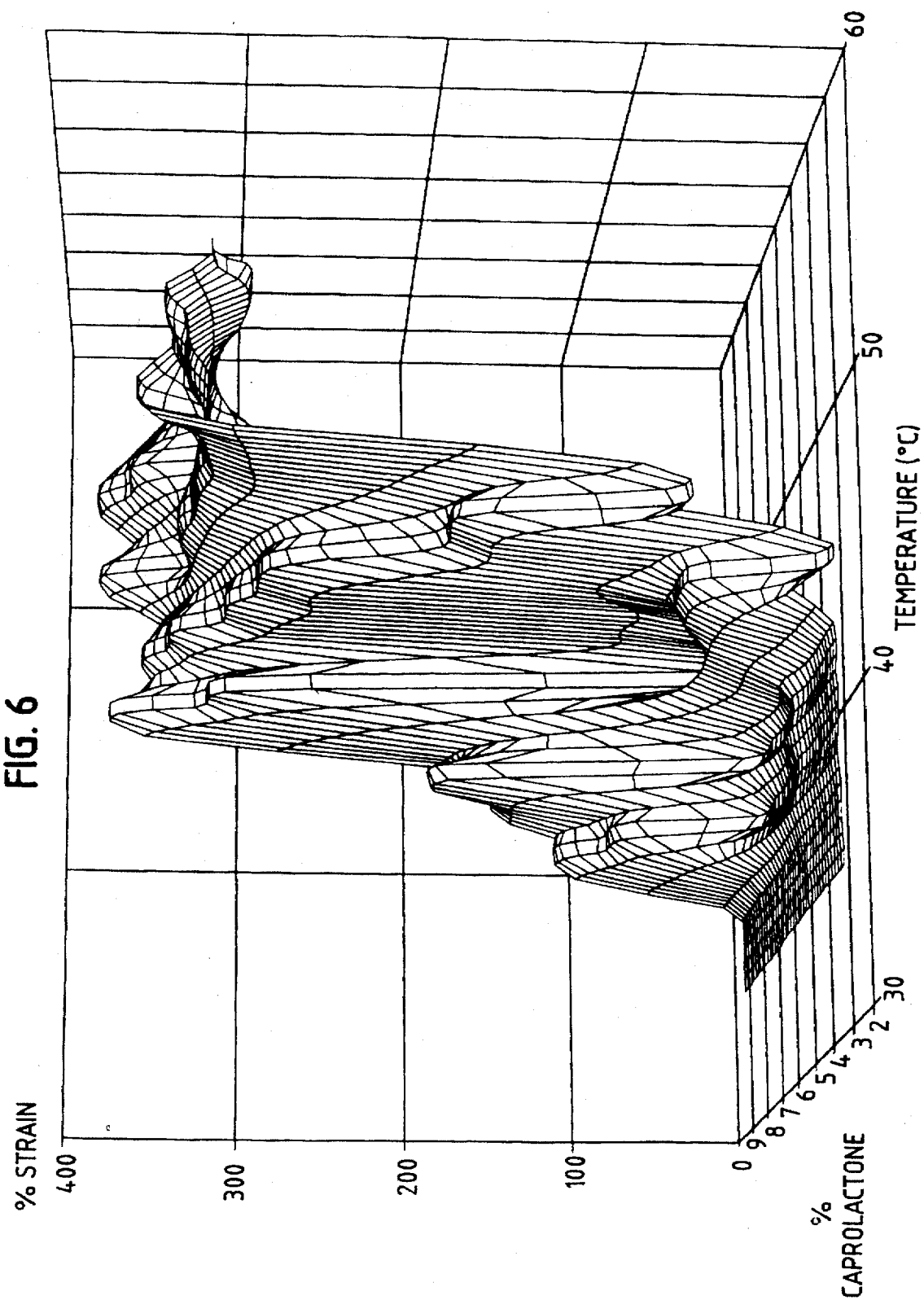
FIGS. 6A and 6B are graphs showing the relationship between caprolactone content in the copolymer of the present invention, temperature, and strain.
Figure 7:
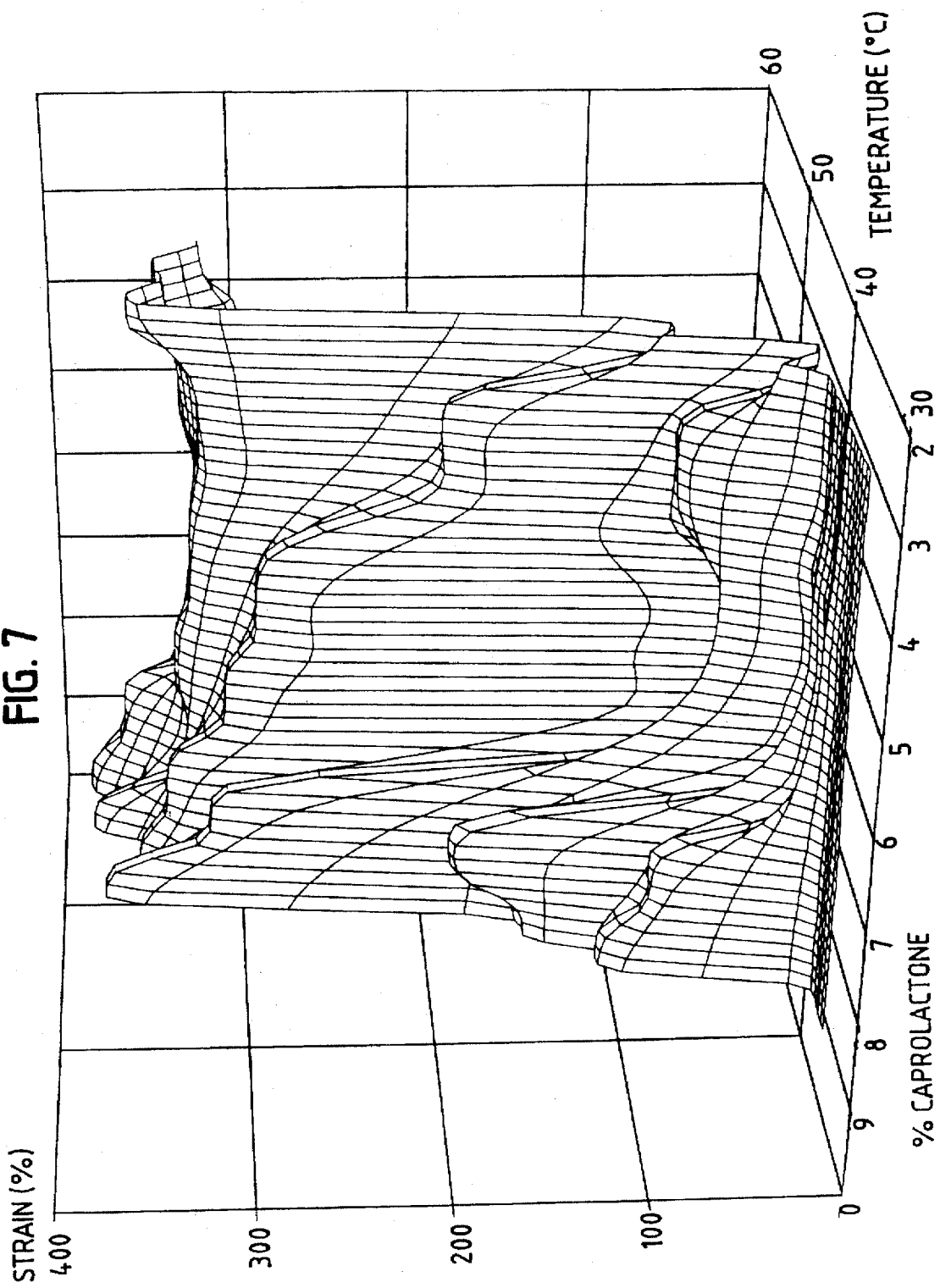

FIG. 6 shows the effects of material composition and temperature on the strain of each of the materials tested. From the data plotted in FIGS. 6A and 6B, it can be seen that the material softens beginning at just above the body temperature (around 38° C.), and that pronounced strain effects can be noted in the copolymer beginning around 40° C. For the reasons noted above, the preferred copolymers exhibit the desired softening behavior beginning at a slightly higher temperature, around 43° C. The figures also reveal that softening occurs at lower temperatures in stents having a higher ε-caprolactone content. Thus, as shown in FIGS. 6A and 6B, at just above body temperature, copolymers having about 3–7 mol % ε-caprolactone exhibit a substantial improvement in elongation up to temperatures of about 55° C. However, it should be understood that copolymers containing up to about 10 mol % ε-caprolactone can be utilized in the invention.

Other biodegradable materials, including copolymers of L-lactide and/or ε-caprolactone, that exhibit similar properties also may be used in the present invention without departing therefrom.

Using the heating techniques described more fully below, the temperature of the polymer can be increased incrementally to a point near the glass-transition temperature of the copolymer, permitting the stent to enter a rubbery phase that takes advantage of a lower elastic modulus. In this phase, the stent may be plastically deformed and the shape stabilized prior to any viscoelastic behavior (such as creep, stress relaxation, strain recovery, or shrinkage) causes the stent to return to its unexpanded shape or to diminish in strength. Following expansion, the polymer is allowed to cool, but because plastic deformation has occurred, the stent remains open. Attempting to expand the stent of the present invention below the glass-transition temperature causes the stent to fracture as a result of its brittle or glassy characteristics below the glass-transition temperature. This could be potentially hazardous, depending upon whether and how the stent fractures as a result of being expanded improperly. Thus, controlled heating and expansion of the stent is important to the invention, as it results in a circumferential drawing of the extruded stent, helping to orient the copolymer molecules, and thereby enhances the modulus and strength of the materials, and ultimately the strength of the stent.

The thermo-mechanical expansion of the stent is considered a processing step occurring in situ and concomitant with deployment. Thermo-mechanical expansion can be viewed as a low temperature drawing of the copolymer tube, which orients the polymer chains and crystallites circumferentially. It is believed that this expansion method, used within the temperature range of about 38°–55° C., results in the preferential orientation of the polymer chains in the amorphous domains of the material. This low temperature drawing substantially increases the elastic modulus and strength of the stent, while stabilizing and maintaining the shape of the expanded stent under external loads. The degree of improvement of these properties depends on the draw ratio, measured as a function of the cross-sectional area of the annulus defining the end of the stent prior to and after expansion. The draw ratio should be above about 1.2, and preferably above about 2.0, and depends on the deployment method and material properties such as initial crystallinity and composition. Desirable draw ratios desired for any particular material can be readily determined by those skilled in the art.

The copolymer used in the present invention may be obtained from Purac Blochem b.v. (Gorinchem, Netherlands) in the nominal ratios specified above. However, because of the presence of unreacted monomers, low molecular weight oligomers, catalysts, and other impurities, it is desirable (and, depending upon the materials used, may be necessary) to increase the purity of the copolymer over that which is commercially available. This purification process yields a copolymer of better-known composition, and therefore increases both the predictability of the mechanical characteristics of the stents made from such materials and the reliability of those stents. In the purification process, the copolymer is dissolved in a suitable solvent, such as methylene chloride. Other suitable solvents include (but are not limited to) ethyl acetate, chloroform, and tetrahydrofuran. The copolymer solution is mixed with a second material that is miscible with the solvent, but in which the copolymer is not soluble, so that the copolymer (but not appreciable quantities of impurities or unreacted monomer) precipitates out of solution. For example, a methylene chloride solution of the copolymer may be mixed with heptane, causing the copolymer to fall out of solution. The solvent mixture then is removed from the copolymer precipitate using conventional techniques.

To form the stent, the copolymer thus prepared is melted at a temperature sufficiently low to minimize polymer degradation in a conventional extruder, and extruded through a die to form a cylindrical tube of the desired wall thickness, inside and outside diameters. The stent may be cut to length on line while hot, or preferably is cooled before cutting. The molten extrudate is cooled preferably by quenching in air or in a temperature-controlled water bath to retain shape and strength-enhancing molecular orientation (along the long axis of the tube) that is introduced by the extrusion process. The extrusion and quenching processes also are used to control the degree of crystallinity of the extruded tube, by locking in the amorphous structure of the extruded polymer, thereby reducing the glass-transition temperature to fall within the desired range. Thus, after the extrusion process, the copolymers are nearly amorphous and have oriented molecular chains.

The stents prepared in this way may be employed in the form in which they were extruded without further processing (i.e., a solid, unperforated tube), or they may incorporate perforations of such size, shape, and frequency so as to enhance thermally-assisted mechanical expansion and allow regeneration of the vascular (or other) tissue. The perforations may be machined using excimer or other lasers, for example, a 193 nanometer argon fluoride laser which is particularly useful to take advantage of certain absorption properties of the L-lactide-ε-caprolactone copolymer. The laser pulses preferably at 40 Hz and 100 mJ/pulse, dispersing energy at 0.7 J/cm$^2$. The invention therefore does not rely upon a woven material to define perforations, which is an advantage because woven material potentially provides a site for thrombogenesis and bacteria colonization. In addition, deployment of woven polymer stents may be elusive, since polymers typically creep during the time when they are stored in a stressed position on the catheter.

As a alternative to the extrusion process just described, the stents may be injection molded using conventional techniques, or may be formed using dip-coating techniques. In these embodiments, any desired perforations may be part of the mold or substrate for coating, or may be micromachined as described above.

The orientation of the polymer chains and crystallites circumferentially, to improve the mechanical properties of the stent, is important. Conventional methods of processing do not allow circumferential orientation of polymer chains and crystal domains (i.e., crystallites). One method to achieve this preferred orientation is to use a glass rod with a crystal-like film of poly(tetrafluoroethylene) (PTFE) deposited mechanically on the surface by known methods. The PTFE film should be deposited circumferentially on a glass rod having an outer diameter equivalent to the desired inner diameter of the stent. The copolymer from which the stent is made is dip coated onto the rod from either the melt or an appropriate solution, such as ethyl acetate or methylene chloride. Additionally, the formed tube may be heat treated to increase its crystallinity; for example, the tube may be heated at about 80°–100° C. for about 5 minutes. However, the crystallinity should remain low enough to allow low temperature expansion of the stent. The fabrication process is believed to orient both the polymer chains and any crystallites formed in the circumferential direction. The "oriented" tube may be processed by laser micromachining as described previously. The thermo-mechanical expansion process further increases the crystallinity, modulus, and strength of the material, and ultimately the strength of the stent.

Still another method for creating materials with oriented polymer chains and crystallites is to fabricate tubes from fibers drawn from the materials described herein. Conventional drawing of fibers aligns the polymer chains and induced crystallites parallel to the direction of fiber length. This process can result in substantial increases in modulus and strength as compared with the non-oriented material. Unlike conventional fiber drawing for self-reinforced composites, fibers for this application would be processed with draw ratios of approximately 20 to 50% of the draw ratio that produced optimal strength and modulus. Fibers of this nature will achieve their optimal strength and modulus when they are expanded in situ, where they will receive the additional drawing. In this technique, fibers may be fabricated into a tube by conventional fiber winding techniques on appropriately sized mandrels, and bonded to make contiguous structures by either solvent vapor fusion, autoclave pressure, vacuum bag, or other conventional techniques. This phase of the processing should not alter the orientation of either the polymer chains or crystallites in the drawn fibers. It is believed that the fibers should be oriented circumferentially so the polymer molecular chains and crystallites are aligned in a similar fashion. Additionally, the formed tube may be heat treated to increase the crystallinity; for example, the tube may be heated at about 80°–100° C. for about 5 minutes. However, the crystallinity should remain low enough to allow expansion of the stent. As above, micromachining then may be performed to introduce any desired perforations.

The stent desirably may incorporate one or more drugs that positively affect healing at the site where the stent is deployed, either incorporated into the copolymer forming the stent, or incorporated into the coating, or both. Such drugs may include antithrombotics (such as anticoagulants), antimitogens, antimitotoxins, antisense oligonucleotides, gene therapy vehicles, nitric oxide, and growth factors and inhibitors. Direct thrombin inhibitors believed to be useful in the invention include Hirudin, Hirugen, Hirulog, PPACK (D-phenylalanyl-L-propyl-L-arginine chloromethyl ketone), Argatreban, and D-FPRCH$_2$Cl (D-phenylalanyl-L-propyl-L-arginyl chloromethyl ketone); indirect thrombin inhibitors include Heparin and Warfarin. Materials capable of β-particle emission also may be useful to inhibit neointima formation. These materials preferably are incorporated in quantities that permit desirable timed release as the stent and/or coating biodegrades. Thus, a stent such as that shown in FIG. 1 is believed to have a useful structural life of about 5–10 weeks, and remains in the body for about 6–9 months without showing major loss of structure. From this information, the quantities of drugs to be included in the copolymer matrix may be readily determined.

A stent prepared according to the present invention preferably also incorporates surface coatings or thin films (about 25 μm thick) designed to reduce the risk of thrombosis and to deliver bioactive agents. These include polymers such as poly(ethylene glycol), poly(vinyl alcohol), poly(vinyl pyrrolidone), poly(methacrylic acid), poly(acrylic acid), and polyacrylamide, that are blended or copolymerized with biodegradable materials; monomers of those materials also may be employed, as may other materials having similar lubricious effects. These materials may be formed as either statistical, block, or graft copolymers or as interpenetrating polymer networks. These materials may serve as drug delivery systems by incorporating effective quantities of pharmacologically active materials in the coating. The film may coat only the surfaces of the stent, or may extend over the micro-machined perforations in the stent to create a combination of a barrier and delivery vehicle.

In making stents according to the invention, it is desirable to control the glass-transition temperature by controlling the copolymer molar ratio and degree of crystallinity. Thus, a stent having lower crystallinity will exhibit a lower glass-transition temperature than with a stent having a higher degree of crystallinity. By controlling the degree of crystallinity, therefore, one may engineer a copolymer that exhibits optimal strain performance within the temperature range above body temperature but below temperatures that will injure tissue surrounding the body lumen in which the stent is to be deployed. As already noted, quenching the extruded hot stent tends to lock in an amorphous structure that desirably reduces the glass-transition temperature of the polymer. Likewise, the stents made according to the invention may be annealed at about 80°–90° C. to increase the crystallinity of the polymer and thereby increase the glass-transition temperature.

In the temperature range described above, the poly(L-lactide-ε-caprolactone) copolymer undergoes thermally-assisted mechanical expansion when exposed to a balloon catheter that is heated in situ during percutaneous insertion of the stent. For example, a conventional balloon catheter used for percutaneous placement of a stent may be filled with a heated contrast medium (at a temperature sufficiently high to heat the stent) that can be injected into the balloon, providing in one medium a method both for expanding the balloon and for transferring heat into the stent. Thus, the contrast medium may be heated in situ using microwave radiation, an RF generator, or a resistance heater, and/or by injecting into the catheter contrast medium that has been heated externally of the body. The contrast medium will need to be heated to about 70° C. to permit sufficient heat to transfer to the stent, and the heated medium will be retained within or circulated through the catheter over a predetermined time period to permit the temperature of the stent to rise above the glass-transition temperature. Heated contrast medium is retained within or circulated through the catheter until the stent rises above the glass-transition temperature. Experimental data shows that sufficient heating occurs in a 37° C. water bath using a saline solution in place of a contrast medium, holding the saline solution at 60° C. for about three minutes.

Instead of a conventional balloon catheter, and depending upon the amount of time needed to heat the stent sufficiently to permit expansion, a perfusion catheter may be used so that the flow of fluids, such as blood, through the body lumen is not interrupted while the stent is being deployed. The perfusion catheter, by permitting blood flow through the affected region, also enhances convection cooling of the catheter and stent.

Thus, to deploy the stent according to the present invention, the stent is placed in its unexpanded state along the periphery of a balloon portion of a balloon catheter, and inserted into the body lumen percutaneously where it travels through the body lumen to the desired site for deployment. The location of the stent at the desired site may be confirmed intraoperatively by radiography. Once at the desired site, the stent is heated for the requisite period of time until its temperature is above the glass-transition temperature of the copolymer, and the balloon then is expanded so that the stent expands to the required size. The heat source then is removed, and the stent cooled by convection and conduction until its temperature is reduced below the glass-transition temperature. (Alternatively, but less desirably, a cooling medium may optionally be introduced through the catheter to cool the stent below the glass-transition temperature.) The stent may also be expanded slightly during this cooling process to fix the circumferential alignment of the polymer chains and prevent strain recovery (shrinkage) of the expanded stent.

One such heating technique is described generally in Lee, U.S. Pat. No. 5,292,321 (which is incorporated by reference herein). However, the positive cooling step required by Lee is not needed in the preferred embodiment of the present invention. Rather convection cooling resulting from blood flow past the stent, and the conduction of heat from the stent into surrounding body tissues, are believed adequate to return the stent to a temperature below the glass-transition temperature.

Another heating technique that may be used in the invention is described generally in Rappaport, U.S. Pat. No. 5,470,352 (which is incorporated by reference herein), as a balloon catheter including a microwave antenna. According to Rappaport, microwave energy first heats low water content materials, leaving high water content materials (such as body tissue) relatively unaffected. Because the stent made according to the invention is made from a low water content material, it will be heated preferentially by such a microwave antenna before body tissues are adversely affected. If such a heating technique is used, it may be desirable to modify the stent to include material enhancing the stent's absorption of microwave radiation.

Alternatively, the microwave frequency and power may be adjusted to preferentially heat the amorphous domains and disordered defects within the crystalline domains. The selective heating may be achieved by using an alternating current field with a high frequency in the microwave region (e.g., 2.45 GHz, 1.5 kW) in a manner known to the art. The advantage of this method of heating is that low temperature microwave heat-drawing is believed to produce similar physical properties at lower temperatures than the other methods described herein, since the amorphous domains are selectively targeted. As previously mentioned, it is believed that the expansion observed within the temperature range of about 38°–55° C. is due to the orientation of the polymer chains in the amorphous domains. This method is believed to allow deployment with minimal transfer of heat to the surrounding tissue, and avoids the need for positive cooling.

Another embodiment uses a balloon that is coated with a microwave sensitive material that selectively heats when exposed to microwave radiation. Heat transferred from this coating raises the temperature of the stent to permit thermomechanical expansion.

In still another embodiment, the balloon may be coated with a dye or similar substance that heats upon exposure to electromagnetic radiation (such as ultraviolet light), which is introduced through the catheter using an optical fiber to heat the stent in situ.

These embodiments reveal that the invention is not limited to a single method of deployment. Other heating and expansion methods besides those described may be used to carry out the invention in practice, however, it should be understood that the invention is limited to thermomechanical deployment techniques.

The present invention has been described with respect to one embodiment, which is not meant to and should not be construed to limit the invention. Those skilled in the art will understand that variations from the embodiments and conditions described herein may be made without departing from the invention as claimed in the appended claims.

What is claimed is:

1. An expandable, biodegradable stent for use within a body lumen comprising a hollow tube made from a copolymer of L-lactide and ε-caprolactone that, in unexpanded form, is of a first diameter sufficient to be retained upon a balloon catheter for placement within the body lumen, and that is not plastically expandable at normal body temperatures, and that is expandable using thermomechanical means at a temperature between about 38°–55° C. when the balloon catheter is inflated to a second diameter sufficient to be retained within the body lumen.

2. The stent of claim 1, wherein the molar ratio of L-lactide to ε-caprolactone is in the range from about 90:10 to about 98:2.

3. The stent of claim 1, wherein the tube is imperforate.

4. The stent of claim 1, wherein the tube is perforated, the perforations placed at a distance relative to each other corresponding to cell ingrowth within the body lumen.

5. The stent of claim 1, wherein the tube is nonwoven.

6. The stent of claim 1, wherein the tube incorporates a radio-opaque material.

7. The stent of claim 1, wherein the tube includes a drug blended with the copolymer.

8. The stent of claim 7, wherein the drug is selected from the group consisting of antithrombotics, anticoagulants, antimitogens, antimitotoxins, antisense oligonucleotides, gene therapy vehicles, nitric oxide, growth factors and inhibitors, Hirudin, Hirugen, Hirulog, PPACK, D-FPRCH$_2$Cl, Heparin, and Warfarin.

9. The stent of claim 1, wherein the tube is coated with a lubricious material.

10. The stent of claim 9, wherein the thickness of the coating is about 25 μm.

11. The stent of claim 9, wherein the coating is blended with a drug.

12. The stent of claim 11, wherein the drug is selected from the group consisting of antithrombotics, anticoagulants, antimitogens, antimitotoxins, antisense oligonucleotides, gene therapy vehicles, nitric oxide, growth factors and inhibitors, Hirudin, Hirugen, Hirulog, PPACK, D-FPRCH$_2$Cl, Heparin, and Warfarin.

13. The stent of claim 9, wherein the coating is a blend of a biodegradable material with lubricious materials selected from the group consisting of poly(ethylene glycol), poly (vinyl alcohol), poly(vinyl pyrrolidone), poly(acrylic acid), poly(methacrylic acid) and polyacrylamide.

14. The stent of claim 9, wherein the coating is a copolymer of a biodegradable material with lubricious materials selected from the group consisting of monomer constituents of poly(ethylene glycol), poly(vinyl alcohol), poly(vinyl pyrrolidone), poly(acrylic acid), poly(methacrylic acid) and polyacrylamide.

15. An expandable, biodegradable stent for use within a body lumen comprising a hollow tube made from a copolymer of L-lactide and ε-caprolactone that, in unexpanded form, is of a first diameter sufficient to be retained upon a balloon catheter for placement within the body lumen, and that is not plastically expandable at normal body temperatures, and that is expandable using thermo-mechanical means at a temperature between about 38°–55° C. when the balloon catheter is inflated to a second diameter sufficient to be retained within the body lumen, further comprising a lubricious coating.

16. The stent of claim 15, wherein the thickness of the coating is about 25 μm.

17. The stent of claim 15, wherein the coating is a blend of a biodegradable material with lubricious materials selected from the group consisting of poly(ethylene glycol), poly(vinyl alcohol), poly(vinyl pyrrolidone), poly(acrylic acid), poly(methacrylic acid) and polyacrylamide.

18. The stent of claim 15, wherein the coating is a copolymer of a biodegradable material with lubricious materials selected from the group consisting of monomer constituents of poly(ethylene glycol), poly(vinyl alcohol), poly (vinyl pyrrolidone), poly(acrylic acid), poly(methacrylic acid) and polyacrylamide.

19. The stent of claim 15, wherein the coating is blended with a drug.

20. The stent of claim 19, wherein the drug is selected from the group consisting of antithrombotics, anticoagulants, antimitogens, antimitotoxins, antisense oligonucleotides, gene therapy vehicles, nitric oxide, growth factors and inhibitors, Hirudin, Hirugen, Hirulog, PPACK, D-FPRCH$_2$Cl, Heparin, and Warfarin.

21. A method for making a stent comprising the steps of:
providing a copolymer of L-lactide and ε-caprolactone that is not expandable at normal body temperatures, and that is thermo-mechanically expandable at a temperature between about 38°–55° C.;
creating a tube from the copolymer having a diameter sufficient to permit the tube to be retained upon an unexpanded balloon catheter for insertion into a body lumen; and cutting the tube into lengths for use as a stent within the body lumen.

22. The method of claim 21, wherein the tube is created by extrusion.

23. The method of claim 21, wherein the tube is created by dip-coating.

24. The method of making a stent of claim 21, wherein the ratio of L-lactide to ε-caprolactone is in the range from about 90:10 to about 98:2.

25. The method of making a stent of claim 21, further comprising the step of micromachining perforations in the tube using a laser.

26. The method of making a stent of claim 21, further comprising the step of incorporating radio-opaque material in the tube.

27. The method of making a stent of claim 21, further comprising the step of blending a drug with the copolymer.

28. The method of making a stent of claim 27, wherein the drug is selected from the group consisting of antithrombotics, anticoagulants, antimitogens, antimitotoxins, antisense oligonucleotides, gene therapy vehicles, nitric oxide, growth factors and inhibitors, Hirudin, Hirugen, Hirulog, PPACK, D-FPRCH$_2$Cl, Heparin, and Warfarin.

29. The method of making a stent of claim 21, further comprising the step of coating the stent with a lubricious material.

30. The method of making a stent of claim 29, further comprising the step of blending a drug with the coating.

31. The method of making a stent of claim 30, wherein the drug is selected from the group consisting of antithrombotics, anticoagulants, antimitogens, antimitotoxins, antisense oligonucleotides, gene therapy vehicles, nitric oxide, growth factors and inhibitors, Hirudin, Hirugen, Hirulog, PPACK, D-FPRCH$_2$Cl, Heparin, and Warfarin.

32. The method of making a stent of claim 29, wherein the coating is a blend of a biodegradable material with a lubricious materials selected from the group consisting of poly(ethylene glycol), poly(vinyl alcohol), poly(vinyl pyrrolidone), poly(methacrylic acid) and polyacrylamide.

33. The method of making a stent of claim 29, wherein the coating is a copolymer of a biodegradable material with a lubricious materials selected from the group consisting of monomer constituents of poly(ethylene glycol), poly(vinyl alcohol), poly(vinyl pyrrolidone), poly(methacrylic acid) and polyacrylamide.

34. A method for making a stent comprising the steps of:
providing a copolymer of L-lactide and ε-caprolactone that is not expandable at normal body temperatures, and that is thermo-mechanically expandable at a temperature between about 38°–55° C.;
creating a tube from the copolymer having a diameter sufficient to permit the tube to be retained upon an unexpanded balloon catheter for insertion into a body lumen;
cutting the tube into lengths for use as a stent within the body lumen; and,
thermo-mechanically expanding the stent within the body lumen to increase the hoop strength of the stent by a sufficient amount to substantially support the body lumen.

35. The method of making a stent of claim 34, wherein the stent is thermo-mechanically expanded so that the draw ratio of the expanded stent is greater than 2.0.

36. A method of deploying an expandable, biodegradable stent within a body lumen, comprising the steps of:

providing percutaneous access to the body lumen;

placing the unexpanded stent, in the form of an unexpanded hollow, nonwoven tube made from a copolymer of L-lactide and ε-caprolactone, upon a balloon portion of a balloon catheter;

transporting the stent to a desired location in the body lumen using the catheter;

heating the stent to a temperature between 38°–55° C., to permit thermo-mechanical expansion of the stent;

expanding the stent to a desired diameter by inflating the balloon catheter;

allowing the stent to cool at least below about 38° C. without applying any positive cooling;

deflating the balloon portion of the catheter; and, withdrawing the catheter.

37. The method of deploying a stent of claim 36, wherein the stent is heated by employing a heated material within the catheter to expand the balloon portion of the catheter.

38. The method of deploying a stent of claim 36, wherein the stent is heated using a heating method selected from the group consisting of microwave heating, DC heating, RF heating, and heating using ultraviolet radiation.

39. The method of deploying a stent of claim 36, wherein the stent is made from a copolymer having a ratio of L-lactide to ε-caprolactone in the range from about 90:10 to about 98:2.

40. The method of deploying a stent of claim 36, wherein the stent is imperforate.

41. The method of deploying a stent of claim 36, wherein the stent is perforated, the perforations placed at a distance relative to each other corresponding to cell ingrowth patterns within the body lumen.

42. The method of deploying a stent of claim 36, wherein the stent is nonwoven.

43. The method of deploying a stent of claim 36, wherein the stent includes a radio-opaque material.

44. The method of deploying a stent of claim 36, wherein the stent includes a drug blended with the copolymer.

45. The method of deploying a stent of claim 44, wherein the drug is selected from the group consisting of antithrombotics, anticoagulants, antimitogens, antimitotoxins, antisense oligonucleotides, gene therapy vehicles, nitric oxide, growth factors and inhibitors, Hirudin, Hirugen, Himlog, PPACK, D-FPRCH$_2$Cl, Heparin, and Warfarin.

46. The method of deploying a stent of claim 36, wherein the stent is coated with a lubricious material.

47. The method of making a stent of claim 46, further comprising the step of blending a drug with the coating.

48. The method of making a stent of claim 47, wherein the drug is selected from the group consisting of antithrombotics, anticoagulants, antimitogens, antimitotoxins, antisense oligonucleotides, gene therapy vehicles, nitric oxide, growth factors and inhibitors, Hirudin, Hirugen, Hirulog, PPACK, D-FPRCH$_2$Cl, Heparin, and Warfarin.

49. The method of deploying a stent of claim 46, wherein the coating is a blend of a biodegradable material with a lubricious materials selected from the group consisting of poly(ethylene glycol), poly(vinyl alcohol), poly(vinyl pyrrolidone), poly(methacrylic acid) and polyacrylamide.

50. The method of deploying a stent of claim 46, wherein the coating is a copolymer of a biodegradable material with a lubricious materials selected from the group consisting of monomer constituents of poly(ethylene glycol), poly(vinyl alcohol), poly(vinyl pyrrolidone), poly(methacrylic acid) and polyacrylamide.

51. A method of deploying an expandable, biodegradable stent within a body lumen, comprising the steps of:

providing percutaneous access to the body lumen;

placing the unexpanded stent, in the form of an unexpanded hollow, nonwoven tube made from a copolymer of L-lactide and ε-caprolactone, upon a balloon portion of a balloon catheter;

transporting the stent to a desired location in the body lumen using the catheter;

heating the stent to a temperature between 38°–55° C., to permit thermo-mechanical expansion of the stent;

expanding the stent to a desired diameter by inflating the balloon catheter so that the draw ratio of the expanded stent is greater than 2.0;

allowing the stent to cool at least below about 38° C.;

deflating the balloon portion of the catheter; and, withdrawing the catheter.

* * * * *